United States Patent [19]

Suzuki et al.

[11] Patent Number: 5,067,814
[45] Date of Patent: Nov. 26, 1991

[54] APPARATUS FOR MEASURING FINE PARTICLE IN LIQUID

[75] Inventors: Riichiro Suzuki, Ikoma; Shigeyuki Akiyama, Ohtsu; Yoshihiro Kubo, Takatsuki, all of Japan

[73] Assignee: Horiba, Ltd., Kyoto, Japan

[21] Appl. No.: 187,595

[22] Filed: Apr. 28, 1988

[30] Foreign Application Priority Data

Jun. 13, 1987 [JP] Japan .................. 62-147530

[51] Int. Cl.⁵ .......................................... G01N 21/53
[52] U.S. Cl. ..................................... 356/339; 250/576
[58] Field of Search ............... 356/336, 339; 250/574, 250/576

[56] References Cited

U.S. PATENT DOCUMENTS 4,178,103 12/1979 Wallace .............................. 356/336
4,226,532 10/1980 Berber et al. .................. 356/339 X

FOREIGN PATENT DOCUMENTS 61-189251 11/1986 Japan .

OTHER PUBLICATIONS

McFadyen et al., "An Automatic Flow Ultramicroscope for Submicron Particle Counting and Size Analysis", *J. Colloid & Interfare Sci.*, vol. 45, No. 3, pp. 573–583, 12/73.

Primary Examiner—Davis L. Willis
Assistant Examiner—Matthew Koren
Attorney, Agent, or Firm—Price, Gess & Ubell

[57] ABSTRACT

An improved apparatus for measuring fine particles in a liquid includes a nozzle for spouting water from within one end of a cell towards an opposite end thereof. An incident light beam traverses the spouted water to scatter light towards a light detection system exteriorly of the cell. The detection system includes a stop for excluding scattered light from being detected and which resulted from fine particles outside a central portion of the spouted liquid.

7 Claims, 2 Drawing Sheets

APPARATUS FOR MEASURING FINE PARTICLE IN LIQUID

BACKGROUND OF THE INVENTION

1. Field of the Invention

The present invention generally relates to an apparatus for measuring fine particles contained in superpurified water and other liquids used for washing and the like in, for example, the manufacturing process of integrated circuits.

2. Description of the Prior Art

Superpurified water and the like containing fine particles at a remarkably small ratio has been used as water for washing and other uses in the manufacturing process of integrated circuits. An apparatus for measuring fine particles contained in such superpurified water and other liquids has been disclosed in, for example, Japanese Utility Model Laid-Open No. 189251/1986.

This conventional apparatus for measuring fine particles contained in liquids comprises a nozzle disposed at one end of a cylindrical cell in a direction of the axial shaft line thereof. The nozzle supplies an inside of the cell with water to be measured and a pipe disposed at the other end of the cylindrical cell discharges the water to be measured. Light-transmitting windows are disposed at opposite positions in a radial direction of the cell; a detection window is disposed at a position meeting at nearly right angles with a line between the windows; and an optical detector is disposed outside of the detection window through an optical system. In addition, a light-emitting means is disposed outside of the light-transmitting window.

In the measurement of fine particles by this conventional apparatus, water to be measured is spouted into the cell from the nozzle and discharged through a discharge pipe. A light, such as a helium-neon laser beam, emitted from the light-emitting means passes through the cell through a pair of light-transmitting windows disposed in an opposite relation, but the light passing through this cell also passes through the water to be measured which was spouted from the nozzle.

Accordingly, if fine particles are contained in the water to be measured, the light is scattered by the fine particles. This light, which was scattered by the fine particles and then transmitted through the detection window, is detected by an optical detector through the optical system. A number and a grain size of the fine particles are measured on the basis of the detected light.

With the conventional apparatus for measuring fine particles, a Gaussian distribution of the laser beam passing through water to be measured and which spouted from the nozzle is strong in a central portion in the radial direction thereof and weak toward both side portions. Thus, the strength of the light scattered by the fine particles, which passed by both side portions of the laser beam, is not proportional to the grain size of the fine particles. Moreover, the strength of the light scattered by the fine particles is inversely proportional to a speed of the fine particles, while a flow rate of water to be measured which spouted from the nozzle is reduced in a circumferential portion of the nozzle in comparison with a central portion of the nozzle.

With the conventional apparatus, the light scattered by the fine particles contained in water to be measured is detected at a position on a side portion of water to be measured which spouted from the nozzle.

Accordingly, since the light scattered by the fine particles contained in both side portions of water to be measured opposite to the optical system is also detected in the partial measurement in which the measurement for both side portions of water to be measured opposite to the optical system is excluded, a problem occurs in that the resolution of grain size is reduced, whereby it is difficult to measure the grain size of the fine particles having a grain size of about 0.4 microns or less.

Accordingly, it has been difficult to presume the kind of fine particles, place where the fine particles are contained and the like, and utilize the measured results for preventing the fine particles from being contained.

SUMMARY OF THE INVENTION

The present invention solves the above-described problems and it is an object of the present invention to provide an apparatus for measuring fine particles contained in liquids and also capable of measuring a grain size distribution of fine particles contained in liquids to be measured with high accuracy.

An apparatus for measuring fine particles contained in liquids according to the present invention comprises a nozzle disposed at one end of a cell supplied with a liquid to be measured and which spouts the liquid to be measured. An incident window is disposed in the cell at a position meeting at nearly right angles with an axial shaft line of the nozzle, in which a light is incident upon the liquid to be measured and which spouted from the nozzle. A light scattered by fine particles contained in the liquid to be measured is detected to measure the fine particles. The present invention is further characterized by a detection window for passing the scattered light therethrough and which is disposed in the cell opposite a spouting port of the nozzle. An optical system and a stop and an optical detector of the scattered light are disposed outside of the detection window.

With this apparatus for measuring fine particles contained in liquids, the liquid to be measured is spouted in the cell from the nozzle. A light, such as a laser beam, is incident upon an inside of the cell through the incident window, the light being passed through the liquid to be measured and which spouted from the nozzle. The light passing through the liquid to be measured collides with the fine particles contained in the liquid to be measured to produce the scattered light. This scattered light is detected by means of the optical detector through the detection window disposed opposite the spouting port of the nozzle. The number and size of the fine particles are thereby measured on the basis of the detected scattered light.

A range of the scattered light, which passed through the detection window and is incident upon the optical detector, is set by means of the stop. The detection window is disposed opposite the spouting port of the nozzle so that only light scattered by fine particles having a small difference in flow rate contained on the central side of a radial section in the liquid to be measured and spouted from the nozzle can be detected. Moreover, light having a small difference in Gaussian distribution existing in the central portion in a radial direction of the light, which passed through the liquid to be measured, can be used as the scattered light. The scattered light having a strength nearly proportional to a size of the fine particles is measured to be able to improve an accuracy of measurement of grain size of fine particles.

BRIEF DESCRIPTION OF THE DRAWINGS

Certain preferred embodiments of the present invention are shown in the drawings, in which.

DESCRIPTION OF THE PREFERRED EMBODIMENTS

The preferred embodiments of an apparatus for measuring fine particles contained in liquids according to the present invention are described below with reference to FIGS. 1 and 2.

Figure 1:
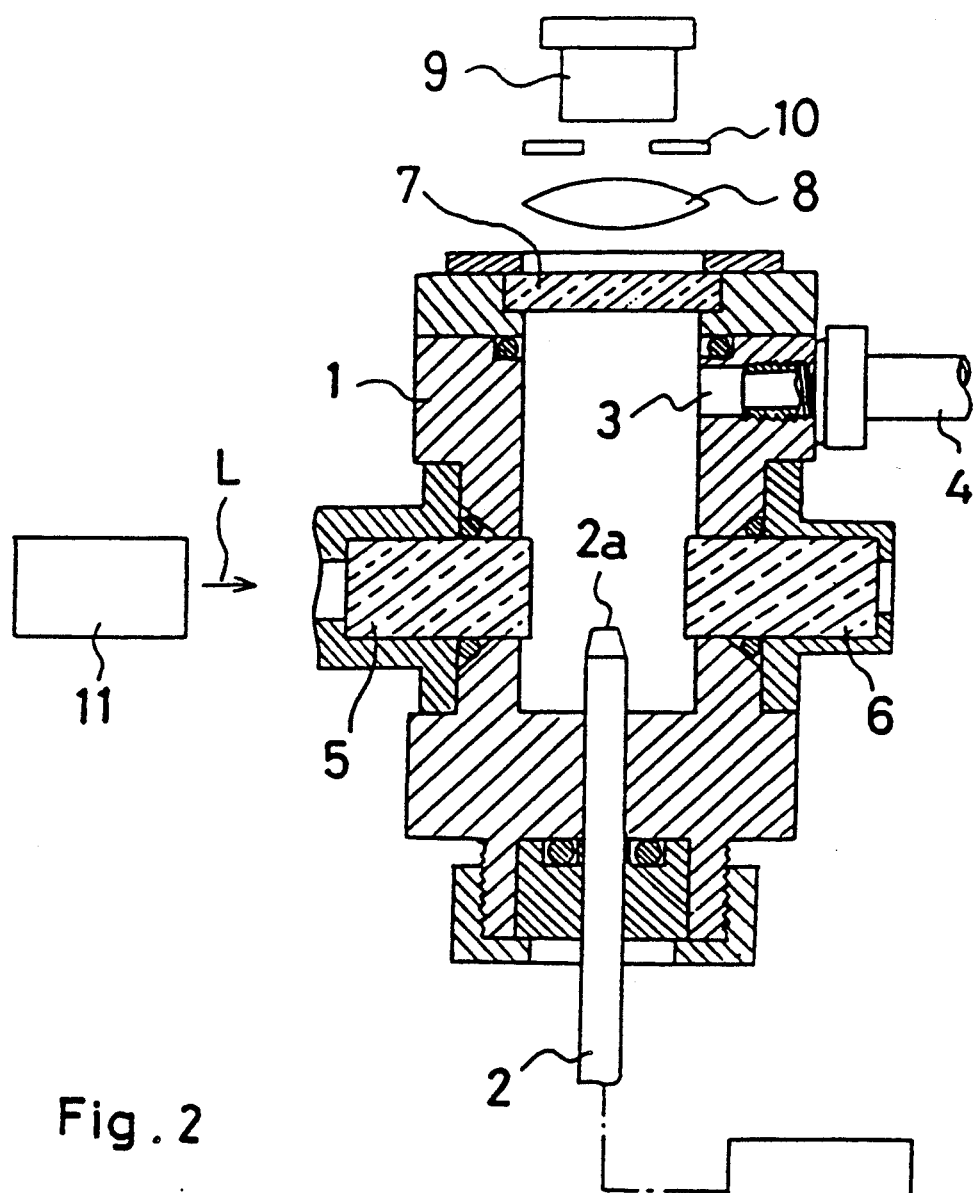
FIG. 1 is a sectional front view according to one embodiment.
Figure 2:
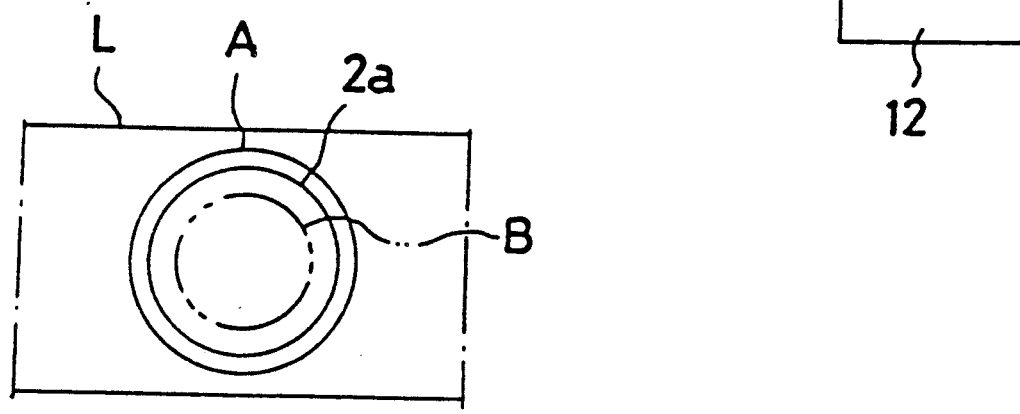
FIG. 2 is an enlarged plan view showing a spouting port of a nozzle according to one embodiment.

Referring now to FIGS. 1 and 2, reference numeral 1 designates a cell formed of metals, such as aluminum, or shading plastics, and to which water to be measured is supplied. The cell 1 is provided with a nozzle 2 inserted in one end thereof for spouting water to be measured. Reference numeral 3 designates an exhaust opening formed in the other end portion of the cell 1 for exhausting water to be measured and connected with an exhaust pipe 4.

Reference numeral 5 designates a light incident window disposed in the cell 1 at a position meeting at right angles with an axial shaft line of the nozzle 2. Reference numeral 6 designates a transmission window disposed in the cell 1 and opposite the light incident window 5. A light incident upon an inside of the cell 1 through the light incident window 5 is exhausted out of the cell 1 through the transmission window 6. The light incident window 5 and the transmission window 6 are disposed so that a light, which passed through them, may pass by the vicinity of a spouting port 2a of the nozzle 2.

In addition, in order to prevent stray light resulting from a difference from water in refractive index on boundary surfaces of the light incident window 5 and the transmission window 6 from having an influence upon measured results, a distance between the nozzle 2 and the light incident window 5 and the transmission window 6, respectively, is set at a slightly larger value.

Reference numeral 7 designates a detection window mounted on the cell 1 and opposite the spouting port 2a of the nozzle 2 for detecting light scattered by fine particles contained in the water to be measured. Reference numeral 8 designates an optical system disposed outside of the detection window 7. Reference numeral 9 designates a light detector for detecting a light which passed through the optical system 8. Reference numeral 10 designates a stop disposed between the optical system 8 and the light detector 9 for adjusting a range of the light, which passed through the optical system 8 and is incident upon the light detector 9. The stop 10 is adapted to be optionally adjustable in caliper. Reference numeral 11 designates a light-emitting means for emitting a light, such as helium-neon laser beam, and reference numeral 12 designates a constant-flow rate means for water to be measured and to be supplied to the nozzle 2.

In the measurement of the fine particles by means of this present apparatus for measuring fine particles contained in liquids, water to be measured is spouted into the cell 1 from the nozzle 2. A pressure of water to be measured is reduced after it is spouted from the nozzle 2 to diffuse water to be measured all over the inside of the cell 1 and exhaust it through the exhaust opening 3. In turn, it flows while almost maintaining a speed distribution within the nozzle 2 and a shape of the spouting port 2a in the vicinity of the spouting port 2a of the nozzle 2.

A light L emitted from the light-emitting means 11 is incident upon the inside of the cell 1 through the light-incident window 5 and exhausted outside of the cell 1 through the transmission window 6. But since the light L passes through water to be measured and which spouted from the nozzle 2 and flows while almost maintaining the shape of the spouting port 2a in the vicinity of the spouting port 2a, if fine particles are contained in water to be measured, the light is scattered by the fine particles.

This scattered light is passed through the detection window 7 and detected by the light detector 9 through the optical system 8 to measure the number and diameter of the fine particles. But since the stop 10 is disposed outside of the detection window 7, the range of the scattered light, which passed through the transmission window 7 and incident upon the light detector 9, can be optionally set by adjusting the stop 10. Moreover, the detection window 7 is disposed opposite the spouting port 2a of the nozzle 2.

Accordingly, as shown in FIG. 2, the scattered light by the fine particles flowing in a circumferential portion of a radial section of water to be measured A, and that spouted from the spouting port 2a of the nozzle 2, in an almost rod-like shape can be removed from a measurement range B so as not to be incident upon the light detector 9 by adjusting the stop 10. That is to say, only the light scattered by the fine particles flowing on the central side having a small difference in velocity of flow of water to be measured and that spouted from the nozzle 2 can be incident upon the light detector 9.

Moreover, as shown in FIG. 2, the measurement range B can be set so that only the scattered light in the central portion having a small difference in Gaussian distribution of the light L may enter the measurement range B. Thus, since the strength of the scattered light incident upon the detector 9 is almost correctly proportional to a size of each fine particle, an accuracy of measurement of diameters of fine particles can be improved to an extent of about 0.2 microns.

Thus, the kind and the type of the fine particles contained in liquids, such as water, can be estimated from the measured results and the fine particles can be prevented from mixing. As a result, the measured results can be effectively utilized.

In addition, a total number of fine particles contained in liquids can be measured rather than a diameter of the fine particles. In that event, since all of the light scattered by all of the fine particles are incident upon the light detector 9 by opening the stop 10 so that the light scattered by all of the fine particles contained in water to be measured may be incident upon the light detector 9, the total number of fine particles can be measured.

Although the stop 10 is adjustable in caliper so as to meet an object of measurement of fine particles contained in water to be measured in this preferred embodiment, a stop 10 having an appointed caliper may be used.

Figure 3:
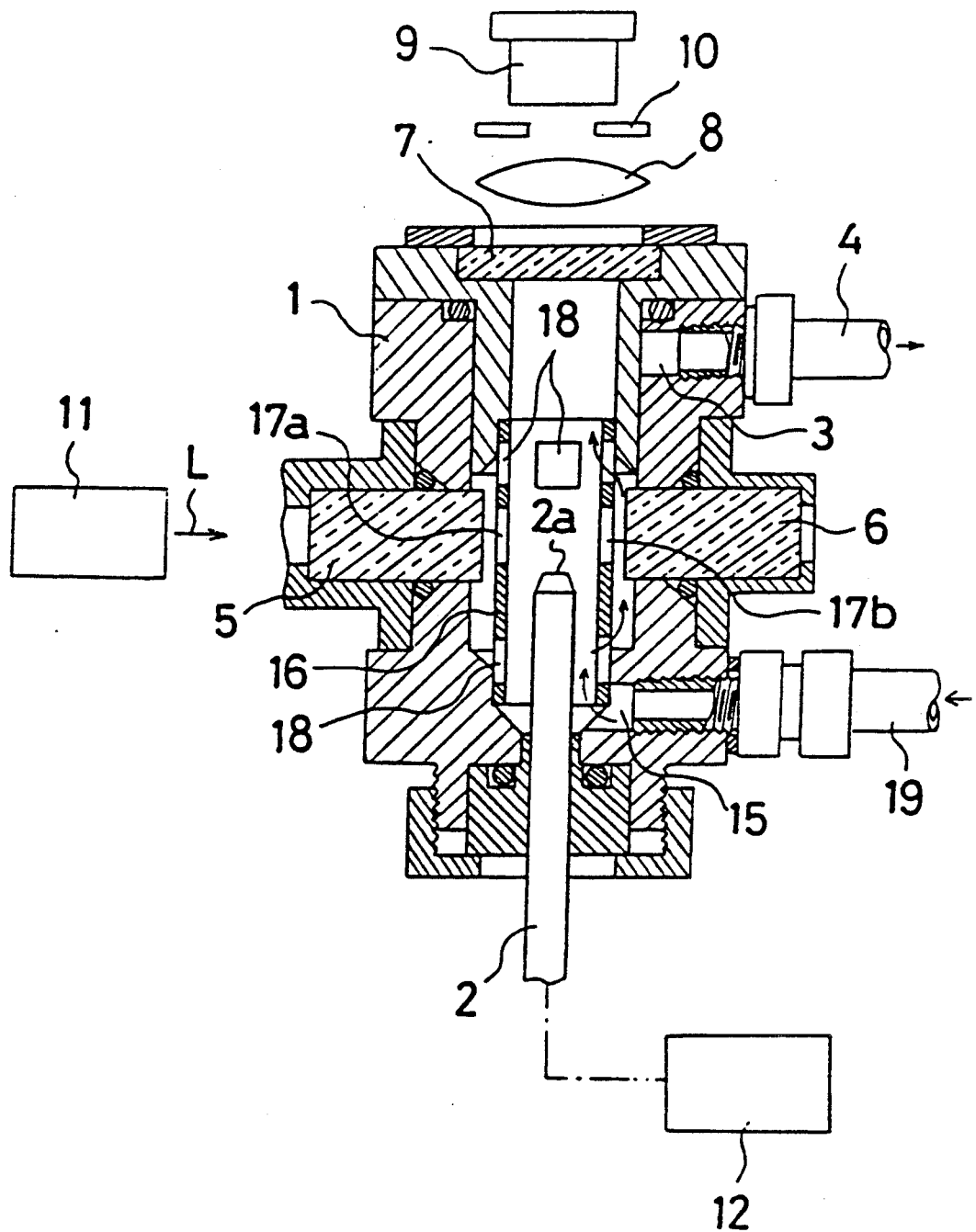
FIG. 3 is a sectional front view showing another preferred embodiment.

FIG. 3 shows another preferred embodiment of the present invention.

An apparatus according to this preferred embodiment reduces an influence of the stray light resulting from the light-incident window and the transmission window even more than in the apparatus according to the preferred embodiment shown in FIG. 1.

Referring to FIG. 3, reference numeral 1 designates a cell; reference numeral 2 designates a nozzle; reference numeral 15 designates a water-pouring port disposed in an end portion of the cell which is provided with the nozzle 2 for pouring a sheath-flow water through the cell 1. Reference numeral 16 designates a rectification cylinder disposed within the cell 1 and almost concentrically with the cell 1 and at an interval from the cell 1. The cylinder 16 communicates with the water-pouring port 15 and the exhaust opening 3, respectively.

The rectification cylinder 16 can be formed of various materials, such as shading plastics and rubbers or aluminum subjected to a black alumite treatment. It is suitable to give it a color, such as black, to reflect only a small quantity of light.

Reference numerals 17a, 17b designate a passing-through hole formed in the rectification cylinder 16 and opposite the light-incident window 5 and the transmission window 6, respectively. Light incident through the light-incident window 5 passes through the passing-through holes 17a, 17b and then goes out of the cell 1 through the transmission window 6. Reference numeral 18 designates a water-passing hole appropriately formed in the rectification cylinder 16. Reference numeral 19 designates a pipe connected with the water-pouring port 15.

Other constructions are the same as in the preferred embodiment shown in FIG. 1 and are marked with the same reference numerals. Consequently, their detailed description is omitted.

With this apparatus according to a second preferred embodiment, a purified sheath-flow water is poured into the cell 1 through the water-pouring port 15 and water to be measured is spouted in the rectification cylinder 16 through the nozzle 2. Water to be measured goes straight under the condition that it is surrounded by the sheath-flow water in the vicinity of the spouting port 2a of the nozzle 2 and then is mixed with the sheath-flow water with a decrease of a pressure thereof followed by exhausting through the exhaust opening 3.

The rectification cylinder 16 prevents stray light, resulting from the refraction on the respective boundary surfaces of the light-incident window 5 and the transmission window 6, from arriving at the detection window 7. The light goes straight on the boundary surface of the sheath-flow water and water to be measured so as not to generate a stray light resulting from refraction. Thus, the influence of the stray light upon the measured results can be reduced to a minimum, whereby an accuracy of measurement of a diameter of fine particles is improved.

With the apparatus for measuring fine particles contained in liquids according to the present invention as above described, the light scattered by the fine particles contained in liquids is detected through the detection window disposed opposite the spouting port of the nozzle, and the range of the scattered light incident upon the light detector through the detection window is set by means of the stop.

Accordingly, only the light scattered by fine particles contained in the range having a small difference in velocity of flow on the central side of the radial section of water to be measured and which spouted from the nozzle can be incident upon the light detector. The range having a small difference in Gaussian distribution on the central side in the radial direction of the light passing through water to be measured, in which the scattering strength is nearly proportional to the diameter of the fine particles, can be used as the scattered light, so that the diameter of the fine particles can also be measured with high accuracy.

What is claimed is:

1. In an apparatus for measuring fine particles contained in liquid, said liquid being spouted inside a housing in a first direction towards a detection system exteriorly of said housing and also having an incident light emitted in a second direction generally transverse to that of the spouted liquid and capable of being scattered by the fine particles, an improved light detection subassembly comprising:
   a nozzle for spouting the liquid in the housing;
   a light incident window, adjacent the nozzle, on the housing;
   a light transmission window, adjacent the nozzle, on the housing;
   a light source for transmitting the incident light respectively through the light incident window, adjacent the nozzle and through the light transmission window;
   a detection window on the housing axially aligned in the first direction with the spouted liquid from the nozzle, and
   a stop means for stopping a portion of total scattered light that could otherwise be detected by said detection system, said scattered light being produced upon said incident light interacting with said fine particles in said spouted liquid, said stop means being disposed exteriorly of said housing and including variable means for varying said portion of total scattered light.

2. The improvement of claim 1 wherein said detection system includes a detector for detecting scattered light and said stop means is intermediate said detector and housing.

3. The improvement of claim 2 wherein said detection system further includes an optical system for focusing said scattered light, and said stop means is intermediate said detector and optical system.

4. The improvement of claim 1 wherein said stop means is also for excluding scattered light resulting from portions of said spouted liquid surrounding a central portion thereof.

5. The improvement of claim 1 further including rectification means for preventing stray light, which results from refraction of light on surfaces of said housing, from being detected by said detection system.

6. The improvement of claim 1 wherein the inside of the housing has a substantially constant diameter.

7. The improvement of claim 6 further including rectification means for eliminating stray refracted light and an exit port for removing spouted liquid in a direction traverse to the first direction.

* * * * *